(12) United States Patent
Quilici

(10) Patent No.: US 10,588,993 B2
(45) Date of Patent: Mar. 17, 2020

(54) UV DOWNLIGHT WITH INTELLIGENT IRRADIANCE CONTROL

(71) Applicant: Michael A. Quilici, Essex, MA (US)

(72) Inventor: Michael A. Quilici, Essex, MA (US)

(73) Assignee: OSRAM SYLVANIA Inc., Wilmington, MA (US)

( * ) Notice: Subject to any disclaimer, the term of this patent is extended or adjusted under 35 U.S.C. 154(b) by 95 days.

(21) Appl. No.: 15/657,340

(22) Filed: Jul. 24, 2017

(65) Prior Publication Data

US 2019/0022263 A1    Jan. 24, 2019

(51) Int. Cl.
| | |
|---|---|
| *A61L 2/24* | (2006.01) |
| *H05B 33/08* | (2020.01) |
| *F21V 14/06* | (2006.01) |
| *F21V 5/00* | (2018.01) |
| *F21V 21/30* | (2006.01) |
| *G01B 11/14* | (2006.01) |
| *A61L 2/10* | (2006.01) |

(Continued)

(52) U.S. Cl.
CPC ............. *A61L 2/24* (2013.01); *A61L 2/084* (2013.01); *A61L 2/10* (2013.01); *F21V 5/007* (2013.01); *F21V 14/06* (2013.01); *F21V 21/30* (2013.01); *G01B 11/14* (2013.01); *H05B 33/0854* (2013.01); *H05B 37/0227* (2013.01); *A61L 2202/11* (2013.01); *A61L 2202/14* (2013.01); *A61L 2202/25* (2013.01); *F21Y 2115/00* (2016.08)

(58) Field of Classification Search
CPC ... A61L 2/24; A61L 2/10; A61L 2/084; H05B 37/0227; H05B 33/0854; F21V 21/30; F21V 5/007; F21V 14/06; G01B 11/14
See application file for complete search history.

(56) References Cited

U.S. PATENT DOCUMENTS 9,801,260 B2 * 10/2017 Anthony ............ H05B 37/0245
2007/0086912 A1    4/2007 Dowling et al.
(Continued)

FOREIGN PATENT DOCUMENTS

WO         2017020028 A1    2/2017

OTHER PUBLICATIONS

Morrish, Ian, International Search Report and Written Opinion of the International Searching Authority, for counterpart application PCT/US2018/042254, dated Oct. 29, 2018, European Patent Office, Rijswijk, The Netherlands, 10 pages.

*Primary Examiner* — Regina M Yoo
(74) *Attorney, Agent, or Firm* — Yutian Ling (57) ABSTRACT

A luminaire for disinfecting a target surface includes a disinfecting light source, a non-disinfecting light source, a beam angle adjustor, a motion sensor, and a distance sensor. The radiance of the disinfecting light is calculated based on detected distance to a target surface and beam angle, and may be selected to achieve a predetermined irradiance of the target surface. If no motion is detected by the motion sensor then the disinfecting light source is set to ON and the non-disinfecting light source is set to OFF. If motion is detected and a beam intercept is not detected by the distance sensor then the disinfecting light source is set to DIM and the non-disinfecting light source is set to ON. If motion is detected and a beam intercept is detected then the disinfecting light source is set to OFF and the non-disinfecting light source is set to ON.

9 Claims, 9 Drawing Sheets

(51) Int. Cl.
*A61L 2/08* (2006.01)
*H05B 37/02* (2006.01)
*F21Y 115/00* (2016.01)

(56) References Cited

U.S. PATENT DOCUMENTS

| | | | |
|---|---|---|---|
| 2009/0267540 A1* | 10/2009 | Chemel | H05B 37/0218 |
| | | | 315/297 |
| 2010/0104471 A1 | 4/2010 | Harmon et al. | |
| 2010/0259931 A1* | 10/2010 | Chemel | F21V 17/02 |
| | | | 362/249.02 |
| 2010/0296285 A1* | 11/2010 | Chemel | F21S 2/005 |
| | | | 362/235 |
| 2012/0235579 A1* | 9/2012 | Chemel | F21S 2/005 |
| | | | 315/152 |
| 2013/0330235 A1 | 12/2013 | Stibich et al. | |
| 2015/0373806 A1 | 12/2015 | Vissenberg et al. | |

\* cited by examiner

UV DOWNLIGHT WITH INTELLIGENT IRRADIANCE CONTROL

TECHNICAL FIELD

The subject matter of this disclosure is generally related to solid-state lighting fixtures, and more particularly to luminaires for disinfecting target surfaces by neutralizing pathogens.

BACKGROUND

Mobile disinfecting luminaires are used to flood spaces such as a hospital rooms with UV-B (ultra-violet light of 280-315 nanometer (nm)) and UV-C (ultra-violet light of 200-280 nm) radiation for disinfection purposes. Such mobile disinfecting luminaires require a relatively brief time, e.g. several minutes, to achieve adequate disinfection but require the room to be evacuated of people. Another type of disinfecting luminaire uses a fixed 405 nm violet light source to provide disinfection without evacuating people from the room. However, such luminaires may require hours to achieve adequate disinfection because their light is less effective at killing pathogens than UV-B and UV-C radiation and is dispersed over a wide area so the irradiance level is relatively low.

SUMMARY

All examples, aspects and features mentioned in this document can be combined in any technically possible way.

Various implementations described herein include an apparatus including a first light source, a beam angle adjustor that controls a beam angle of the first light source and indicates the beam angle, a distance sensor that indicates a distance from the first light source to a target surface that is irradiated by the first light source, and a processor that calculates and sets a radiance of the first light source based on the beam angle indicated by the beam angle adjustor and the distance from the first light source to the target surface indicated by the distance sensor in order to achieve a predetermined irradiance of the target surface. In some embodiments, the luminaire further includes a motion sensor that indicates sensed motion in a volume of space that is greater than a volume of space in which the first light source emits light, and the processor is responsive to an indication of motion from the motion sensor to partially reduce the radiance of the first light source. In some embodiments, the processor is responsive to detection of a change in the distance detected by the distance sensor to zero the radiance of the first light source. In some embodiments, the luminaire further includes a power supply, and the processor controls the power supply to set the radiance of the light source. In some embodiments, the first light source is a disinfecting light source including a plurality of light emitting diodes (LEDs) that emit at least one of: UV-C radiation (100 nm-280 nm); UV-B radiation (280 nm-315 nm); UV-A radiation (315 nm-400 nm); violet light, and blue light. In some embodiments, the luminaire further includes a power supply, and the processor controls the power supply to selectively power and de-power individual LEDs in the plurality of LEDs of the disinfecting light source. In some embodiments, the luminaire includes a second light source that includes a plurality of LEDs that emit white light. In some embodiments, the luminaire further includes a motion sensor that indicates sensed motion in a volume of space that is greater than a volume of space in which the first light source emits light, and the processor is responsive to an indication of motion from the motion sensor to partially reduce the radiance of the first light source and change radiance of the second light source from an OFF state to an ON state.

Various implementations described herein include a method of operating a luminaire that includes a first light source, a beam angle adjustor, a distance sensor, and a processor. The method includes controlling, by the beam angle adjustor, a beam angle of the first light source and indicating the beam angle, indicating, by the distance sensor, a distance from the first light source to a target surface that is irradiated by the first light source, and calculating and setting, by the processor, a radiance of the first light source based on the beam angle indicated by the beam angle adjustor and the distance from the first light source to the target surface indicated by the distance sensor in order to achieve a predetermined irradiance of the target surface. In some embodiments, the luminaire further includes a motion sensor and the method further includes indicating, by the motion sensor, sensed motion in a volume of space that is greater than a volume of space in which the first light source emits light, and partially reducing, by the processor, the radiance of the first light source in response to the sensed motion from the motion sensor. In some embodiments, the method further includes zeroing, by the processor, the radiance of the first light source in response to detection of a change in the distance detected by the distance sensor. In some embodiments, the luminaire further includes a power supply and the method further includes controlling, by the processor, the power supply to set the radiance of the first light source. In some embodiments, the first light source includes a plurality of light emitting diodes (LEDs) that emit at least one of: UV-C radiation (100 nm-280 nm); UV-B radiation (280 nm-315 nm); UV-A radiation (315 nm-400 nm); violet light, and blue light. In some embodiments, the luminaire further includes a power supply and the method further includes controlling, by the processor, the power supply to selectively power and de-power individual LEDs of the plurality of LEDs. In some embodiments, the luminaire further includes a second light source that includes a plurality of LEDs that emits white light when in an ON state. In some embodiments, the luminaire further includes s a motion sensor and the method further includes indicating, by the motion sensor, sensed motion in a volume of space that is greater than a volume of space in which the first light source emits light, and partially reducing, by the processor, the radiance of the first light source and changing radiance of the second light source from an OFF state to an ON state in response to the sensed motion from the motion sensor.

Various implementations described herein include an apparatus including a first light source that emits disinfecting light, a second light source that emits white light, a beam angle adjustor that controls a beam angle of the first light source and indicates the beam angle, a distance sensor that indicates a distance from the first light source to a target surface that is irradiated by the first light source, and a processor that calculates and sets a radiance of the first light source based on the beam angle indicated by the beam angle adjustor and the distance from the first light source to the target surface indicated by the distance sensor in order to achieve a predetermined irradiance of the target surface.

In some embodiments, the apparatus further includes a motion sensor that indicates sensed motion in a volume of space that is greater than a volume of space in which the first light source emits light, and in the absence of sensed motion the processor places the first light source in an ON state and the second light source in an OFF state. In some embodiments, the processor responds to an indication of motion from the motion sensor by partially reducing the radiance of the first light source and changing radiance of the second light source from an OFF state to an ON state. In some embodiments, the processor responds to detection of a change in the distance detected by the distance sensor to place the first light source in an OFF state.

These and other features will be understood better by reading the following detailed description, taken together with the figures herein described. The accompanying figures are not intended to be drawn to scale. Each identical or nearly identical component that is illustrated in various figures may be represented by a like numeral. For purposes of clarity, not every component may be labeled in every figure.

DETAILED DESCRIPTION

Some aspects, features and implementations described herein may include machines such as computers, electronic components, optical components, and computer-implemented processes. It will be apparent to those of ordinary skill in the art that the computer-implemented processes may be stored as computer-executable instructions on a non-transitory computer-readable medium. Furthermore, it will be understood by those of ordinary skill in the art that the computer-executable instructions may be executed on a variety of tangible processor devices. For ease of exposition, not every device or component that may be part of a computer or data storage system is described herein. Those of ordinary skill in the art will recognize such devices and components in view of the teachings of the present disclosure and the knowledge generally available to those of ordinary skill in the art. The corresponding machines and processes are therefore enabled and within the scope of the disclosure.

Figure 1:
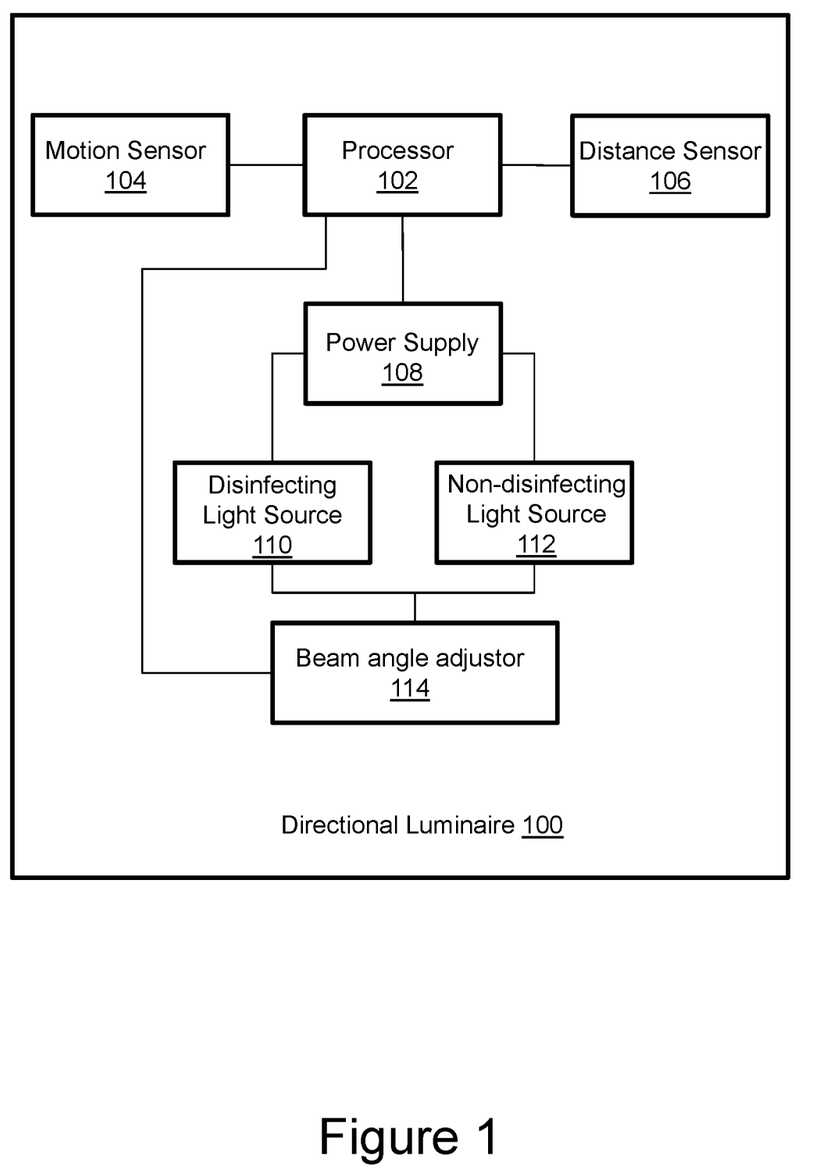
FIG. 1 is a block diagram of a luminaire with irradiance control in accordance with various embodiments.

FIG. 1 is a block diagram of a luminaire 100 with irradiance control in accordance with various embodiments. In some implementations the luminaire 100 may be implemented as a type of downlight for disinfecting a target surface. The luminaire 100 may include a processor 102, a motion sensor 104, a distance (proximity) sensor 106, a power supply 108, a disinfecting light source 110, a non-disinfecting light source 112, and a beam angle adjustor 114.

The processor 102 may include a general purpose processor, a special purpose processor such as an ASIC (application-specific integrated circuit) or FPGA (field programmable gate array), or combinations thereof, for example and without limitation, any of which may include non-transitory computer-readable memory. The motion sensor 104 may include PIR (passive infrared) sensors, MW (microwave) sensors, ultrasonic sensors, vibration sensors, and combinations thereof, for example and without limitation. The distance sensor 106 may include an ultrasonic time-of-flight sensor, optical time-of-flight, IR (infrared) sensors using IR triangulation, for example and without limitation. The disinfecting light source 110 may include LEDs that emit light in any of a variety of wavelengths in bands including but not limited to UV-C (100 nm-280 nm), UV-B (280 nm-315 nm), UV-A (315 nm-400 nm), violet light, and blue light, e.g. and without limitation 200 nm, 254 nm, 265 nm, 280 nm, 311 nm, 365 nm, and 405 nm, for example and without limitation. 265 nm is at the peak of the germicidal effectiveness curve and may be the optimal wavelength to use in UV-C for killing viruses and bacteria. 365 nm can be used for disinfection with a chemical called a photosensitizer, e.g. riboflavin (vitamin b2), to kill bacteria and viruses. The non-disinfecting light source 112 may emit white light, for example and without limitation. The beam angle adjustor 114 may include, for example and without limitation, a lens that refracts the light emitted by the disinfecting light source 110 and possibly the non-disinfecting light source 112, a movable parabolic or elliptical reflector, a rotating array of lenses (lenslets), an electro-optical device including but not limited to an electronically deformable lens or MEMS-based DMD (micro electro-mechanical system-based digital micro-mirror) reflector, selectively powering and de-powering LEDs of a matrix or array, or any other suitable technology. The beam angle adjustor 114 may be operated manually, electronically, or mechanically.

The processor 102 may be responsive to inputs from the distance sensor 106 and beam angle adjustor 114 to calculate and set the radiance level of the disinfecting light source 110 in order to achieve a predetermined irradiance of a target surface. This may be accomplished, for example and without limitation, by the processor controlling the power supply 108 to adjust the radiance of the LEDs of the disinfecting light source 110 and possibly the non-disinfecting light source 112, or by the processor 102 selectively powering and de-powering individual LEDs of the disinfecting light source 110 and possibly the non-disinfecting light source 112 via the power supply 108. Further, the processor 102 may be responsive to inputs from the motion sensor 104 and distance sensor 106 to change the ON/OFF/DIM state of the disinfecting light source 110 and the non-disinfecting light source 112. In general, the motion sensor 104 detects motion in a greater volume of space than is irradiated by the disinfecting light source 110 as controlled by the beam angle adjustor 114. Consequently, the presence of a person in an area near to the emitted disinfecting light may be detected before the person is irradiated by the disinfecting light. In general, the distance sensor 106 detects objects in a volume of space that is irradiated by the disinfecting light source. Consequently, the presence of a person being irradiated by the disinfecting light may be detected by the distance sensor 106, e.g. via a beam intercept indicated by a change in the detected distance.

Figure 2:
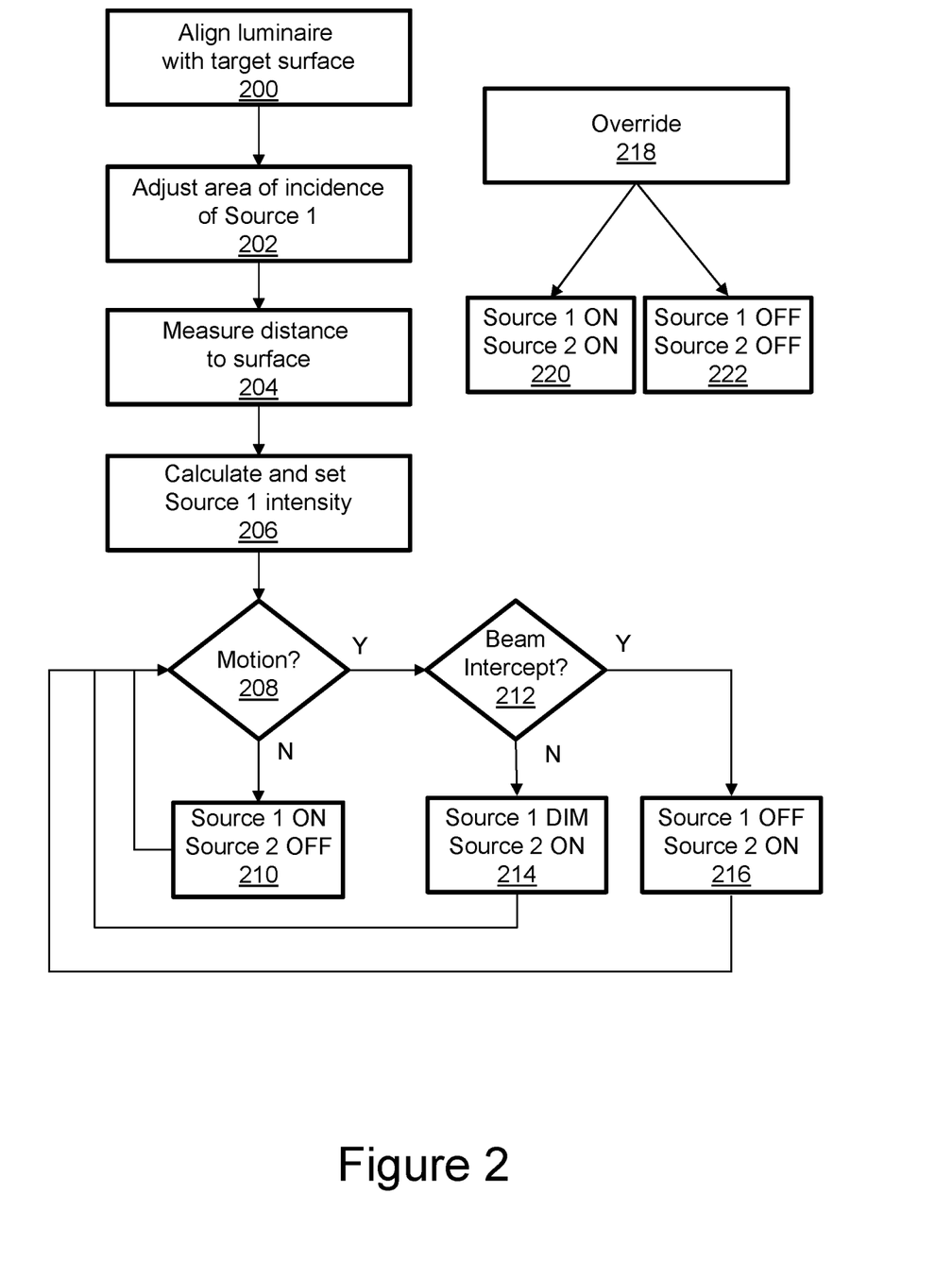
FIG. 2 illustrates a method of irradiance control for the luminaire of FIG. 1 in accordance with various embodiments.

FIG. 2 illustrates a method of irradiance control for the luminaire of FIG. 1 in accordance with various embodiments. The method may be performed by one or more components in the luminaire 100 as illustrated in FIG. 1, such as the processor 102, the beam angle adjustor 114, the motion sensor 104, and the distance sensor 106. The luminaire is aligned with the target surface to be treated as indicated in block 200. For example and without limitation, the disinfecting light source (denoted as "Source 1" in FIG. 2) may be manually, electronically or mechanically pointed directly at a surface to be disinfected. The area of incidence of the disinfecting light source is adjusted as indicated in block 202 by using the beam angle adjustor. For example and without limitation, the area of incidence may be adjusted to roughly coincide with the area of the surface to be disinfected by adjusting the beam angle of the disinfecting light source with the beam angle adjustor. The emitted disinfecting light may pass through a volume of space having a conical, cylindrical or other shape, a cross-section of which does not necessarily match the target surface, so the emitted disinfecting light does not necessarily coincide exactly with the target surface. The distance from the luminaire to the target surface is measured with the distance sensor as indicated in block 204. The distance to the target surface and the beam angle may be used to calculate and set the radiance of the disinfecting light source as indicated in block 206. For example, the radiance may be set to achieve a predetermined $W/m^2$ irradiance of the target surface. At this point the luminaire may be considered ready for use in disinfecting the target surface.

During operation, if no motion is detected by the motion sensor as indicated in block 208 then the disinfecting light source is set to ON (maximum radiance) and the non-disinfecting light source (denoted as "Source 2" in FIG. 2) is set to OFF (no radiance) as indicated in block 210. If motion is detected as indicated in block 208 and a beam intercept (e.g., a person entering the area of the disinfecting beam) is not detected by the distance sensor as indicated in block 212 then the disinfecting light source is set to DIM (less than maximum radiance, but not OFF) and the non-disinfecting light source is set to ON as indicated in block 214. If motion is detected as indicated in block 208 and a beam intercept is detected as indicated in block 212 then the disinfecting light source is set to OFF and the non-disinfecting light source is set to ON as indicated in block 216. An override input as indicated in block 218 can be used to set both the disinfecting light source and the non-disinfecting light source to ON as indicated in block 220, or to set both the disinfecting light source and the non-disinfecting light source to OFF as indicated in block 222. In some embodiments, the processor may also selectively power and de-power individual LEDs of the disinfecting light source and possibly the non-disinfecting light source based on inputs of the motion sensor and/or distance sensor.

Although no specific advantages are necessarily associated with implementations, adjusting the area of incidence of the disinfecting light source by changing the beam angle may provide greater irradiance of the target surface for a given source radiance, and thus achieve adequate disinfection more quickly relative to fixed beam angle luminaires that disperse light over an area greater than the target surface. Moreover, setting a radiance value based on distance and beam angle can provide a predetermined irradiance of the target surface, and thus a more predictable disinfection time. Adjusting the radiance of the disinfecting light based on motion and beam intercept may help to prevent people from being undesirably irradiated. For example, the disinfecting light may dim when a person is nearby but not in the direct path of the disinfecting light, and the disinfecting light may be turned OFF when a person is in the direct path of the disinfecting light. In some implementations a UV-C or violet light may be used to provide quicker disinfection than the current state of the art luminaires without the need to evacuate the nearby area of people. However none of the advantages described above should be viewed as limiting.

Figure 3:
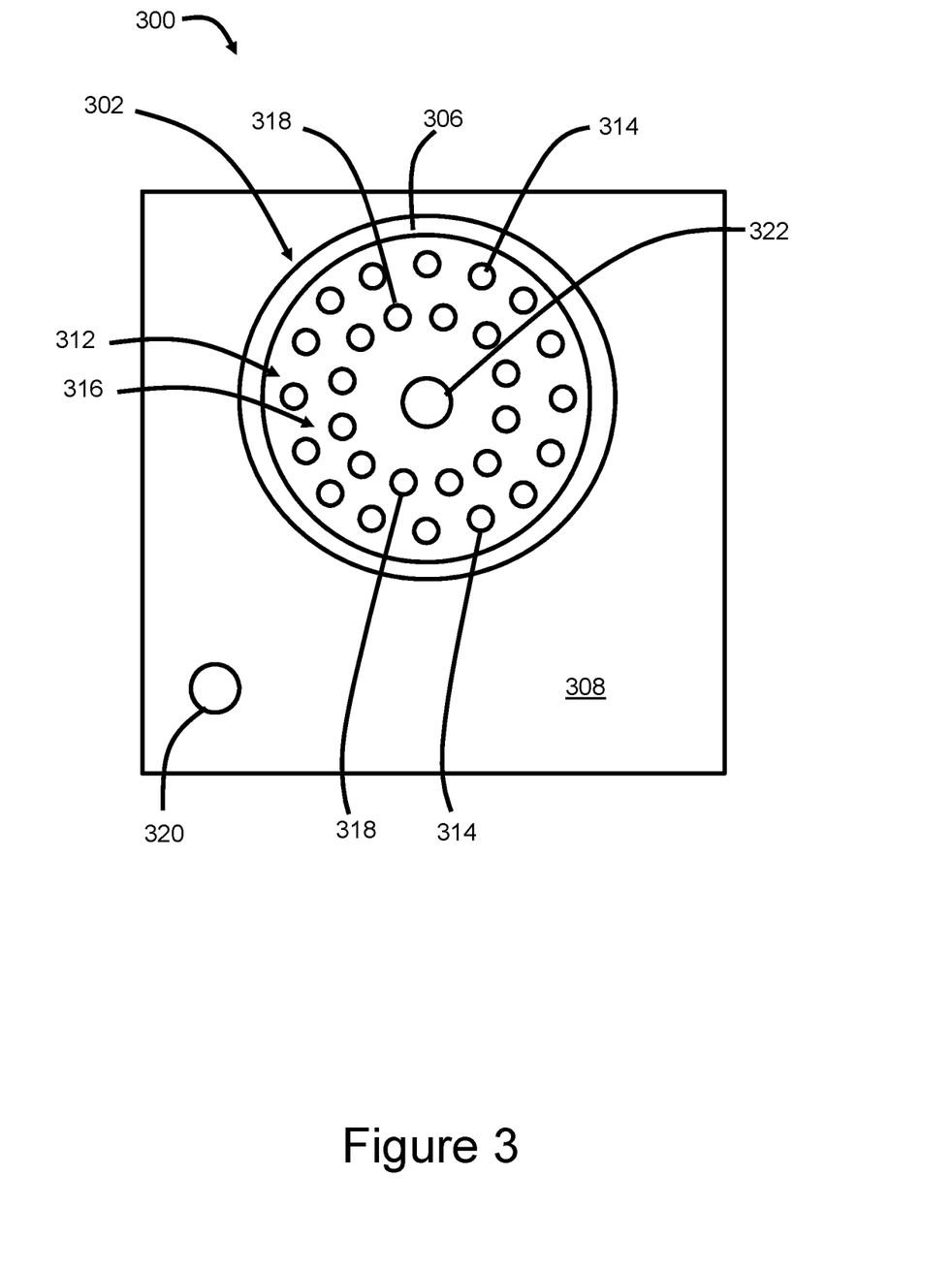
FIGS. 3 and 4 illustrate a recessed lighting implementation of the luminaire of FIG. 1 in accordance with various embodiments.
Figure 4:
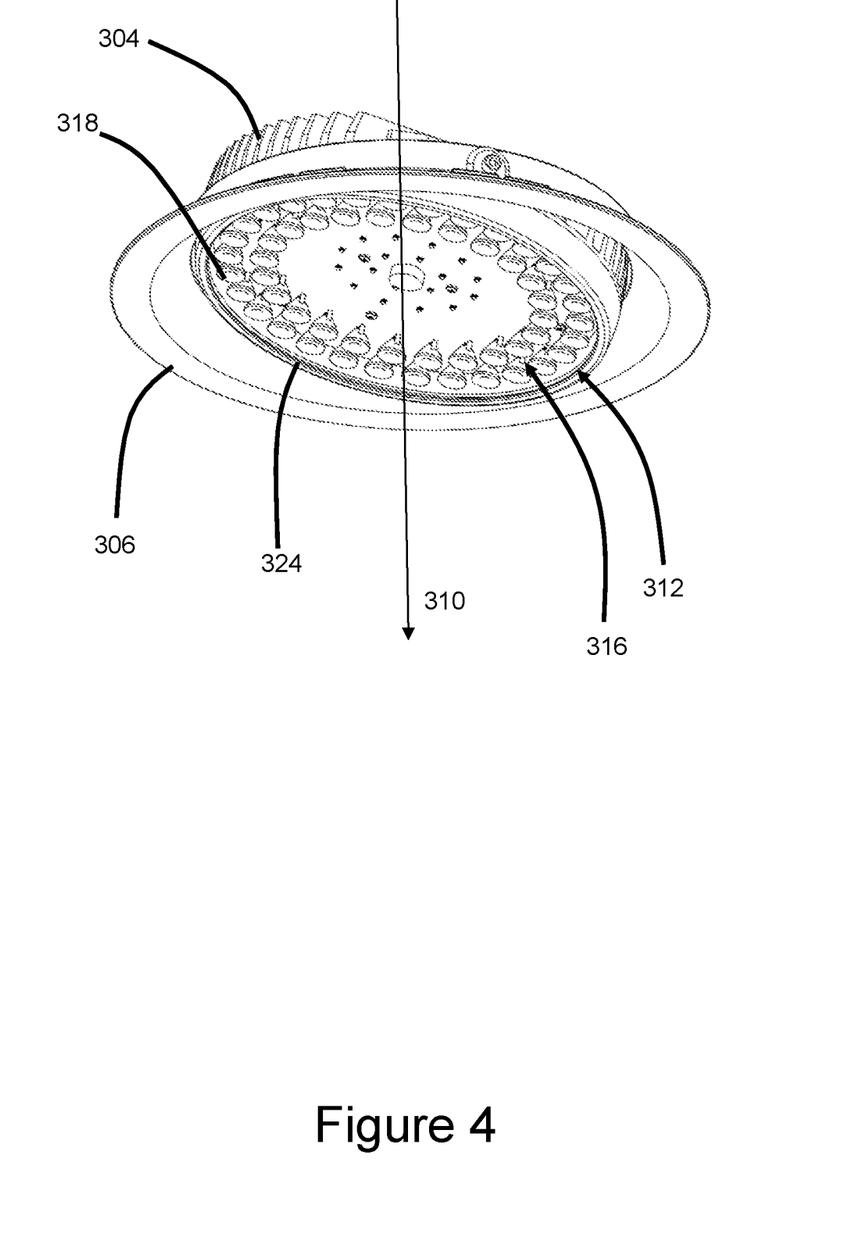

FIGS. 3 and 4 illustrate a recessed lighting implementation of the luminaire of FIG. 1 in accordance with various embodiments. The illustrated luminaire 300 includes a matrix of LEDs 302 in a housing 304 that pivots and rotates relative to a flange 306 that is connected to a flat panel 308. The flat panel 308 may be sized to replace a standard ceiling panel of a suspended ceiling, although this should not be viewed as limiting. The housing 304, and thus the LED matrix, may be rotatable through 360 degrees and pivot to some angle, e.g. and without limitation +/−20 degrees, relative to an axis 310 that is normal to the panel. In the specifically illustrated example the LED matrix includes a first (outer) ring 312 of disinfecting light source LEDs 314 and a second (inner) ring 316 of non-disinfecting light source LEDs 318. A motion sensor 320 and a distance sensor 322 may be mounted through the panel or incorporated into the housing or LED matrix. The luminaire 300 may be aligned with the target surface by swiveling and pivoting the housing to point the matrix of LEDs 302 toward the target surface. The area of incidence of the emitted light may be adjusted by changing the beam angle with a lens 324 that is disposed between the LEDs and the target surface, e.g. and without limitation connected to the housing 304 in which the LED matrix is disposed. The distance sensor 322 may be used both to measure the distance to the target surface and to detect a beam intercept, e.g. by a person, based on a change in the measured distance.

Figure 5:
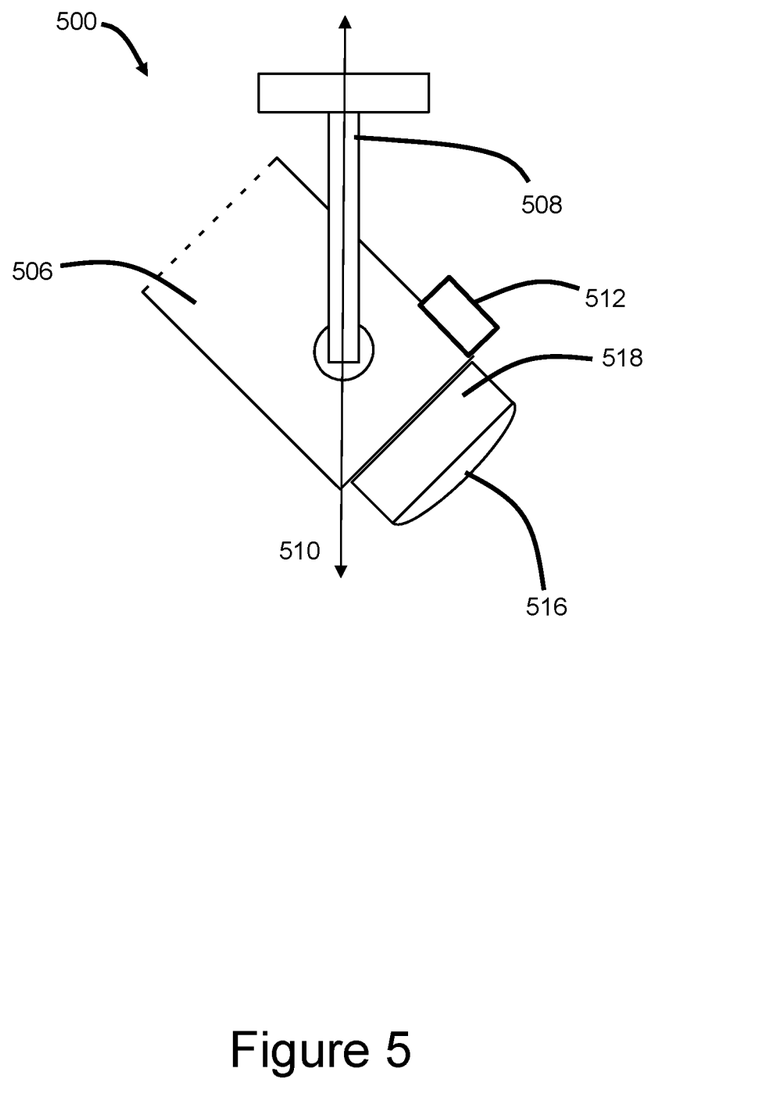
FIGS. 5 and 6 illustrate a track lighting implementation of the luminaire of FIG. 1 with a movable lens in accordance with various embodiments.
Figure 6:
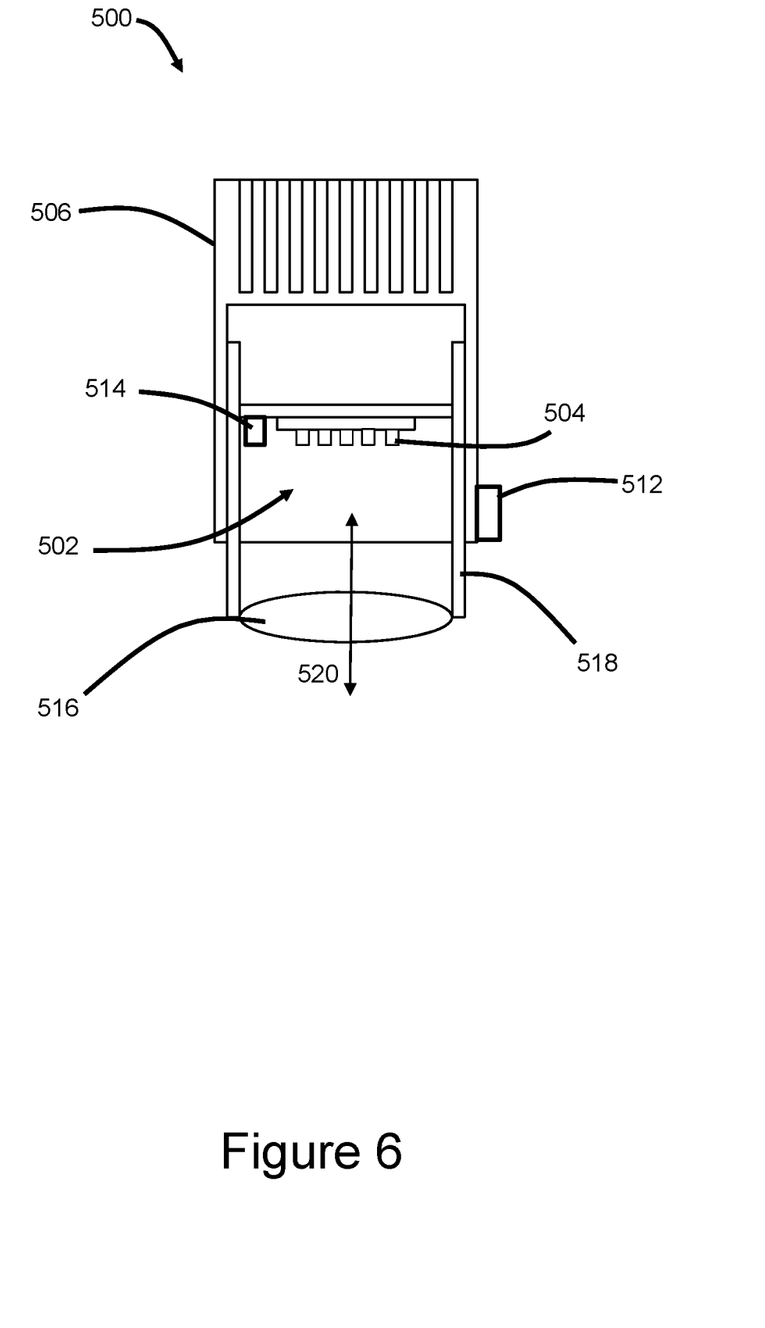

FIGS. 5 and 6 illustrate a track lighting implementation of the luminaire of FIG. 1 with a movable lens in accordance with various embodiments. The illustrated luminaire 500 includes a matrix 502 of LEDs 504 in a housing 506 that pivots and rotates relative to a track mount 508. The housing 506, and thus the LED matrix, may be rotatable through 360 degrees and pivot to some angle, e.g. and without limitation +/−90 degrees, relative to an axis 510 that is normal to the ceiling. A motion sensor 512 and a distance sensor 514 may be incorporated into the housing 506 or LED matrix 502. The luminaire 500 may be aligned with the target surface by swiveling and pivoting the housing 506 to point the matrix of LEDs toward the target surface. The area of incidence of the emitted light may be adjusted with a movable lens 516 that is disposed between the LEDs and the target surface, e.g. and without limitation on disposed lens mount 518 coupled with the housing 506. The distance between the lens 516 and the LEDs 504 may be adjusted by sliding the lens mount 518 relative to the housing 506 along axis 520. The distance sensor may be used both to measure the distance to the target surface and to detect a beam intercept, e.g. by a person, based on a change in the measured distance.

Figure 7:
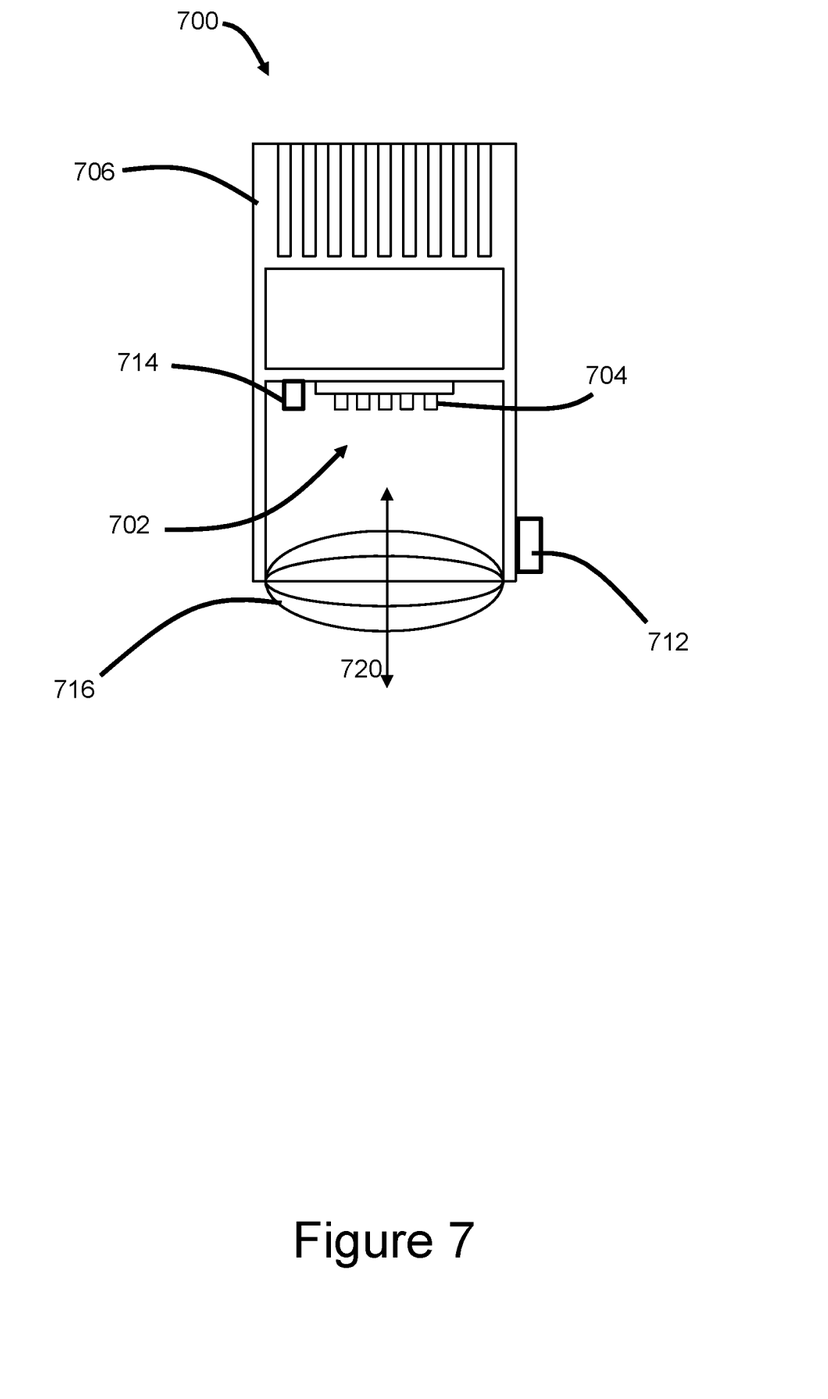
FIG. 7 illustrates a track lighting implementation of the luminaire of FIG. 1 with a deformable lens in accordance with various embodiments.

FIG. 7 illustrates a track lighting implementation of the luminaire of FIG. 1 with a deformable lens in accordance with various embodiments. The illustrated luminaire 700 includes a matrix 702 of LEDs 704 in a housing 706 that pivots and rotates relative to a track mount. The housing 706, and thus the LED matrix, may be rotatable through 360 degrees and pivot to some angle, e.g. and without limitation +/−90 degrees, relative to an axis that is normal to the ceiling. A motion sensor 712 and a distance sensor 714 may be incorporated into the housing 706 or LED matrix 702. The luminaire may be aligned with the target surface by swiveling and pivoting the housing 706 to point the matrix of LEDs toward the target surface. The area of incidence of the emitted light may be adjusted with a deformable lens 716 that is disposed between the LEDs and the target surface, e.g. and without limitation disposed at a distal end of the housing 706. The shape of the deformable lens 716 may be adjusted, e.g. and without limitation in an axis 720. The distance sensor 714 may be used both to measure the distance to the target surface and to detect a beam intercept, e.g. by a person, based on a change in the measured distance.

Figure 8:
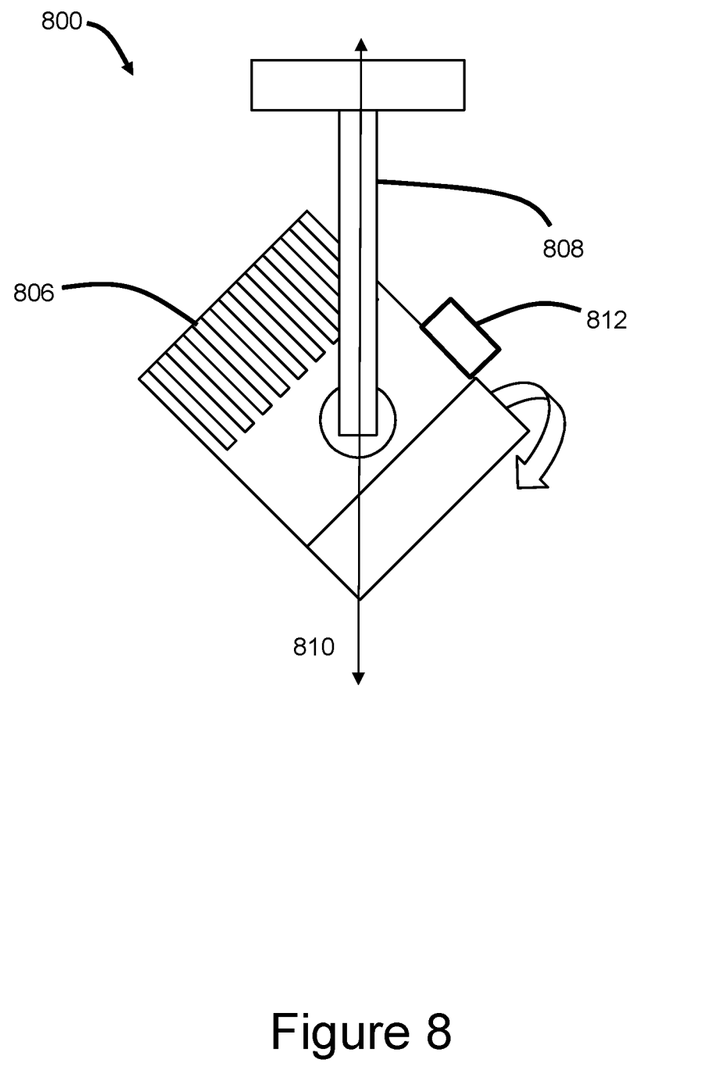
FIGS. 8 and 9 illustrate a track lighting implementation of the luminaire of FIG. 1 in which the beam angle adjustor is implemented by rotating an array of lenses with respect to a fixed array or matrix of LEDs (light emitting diodes) in accordance with various embodiments.
Figure 9:
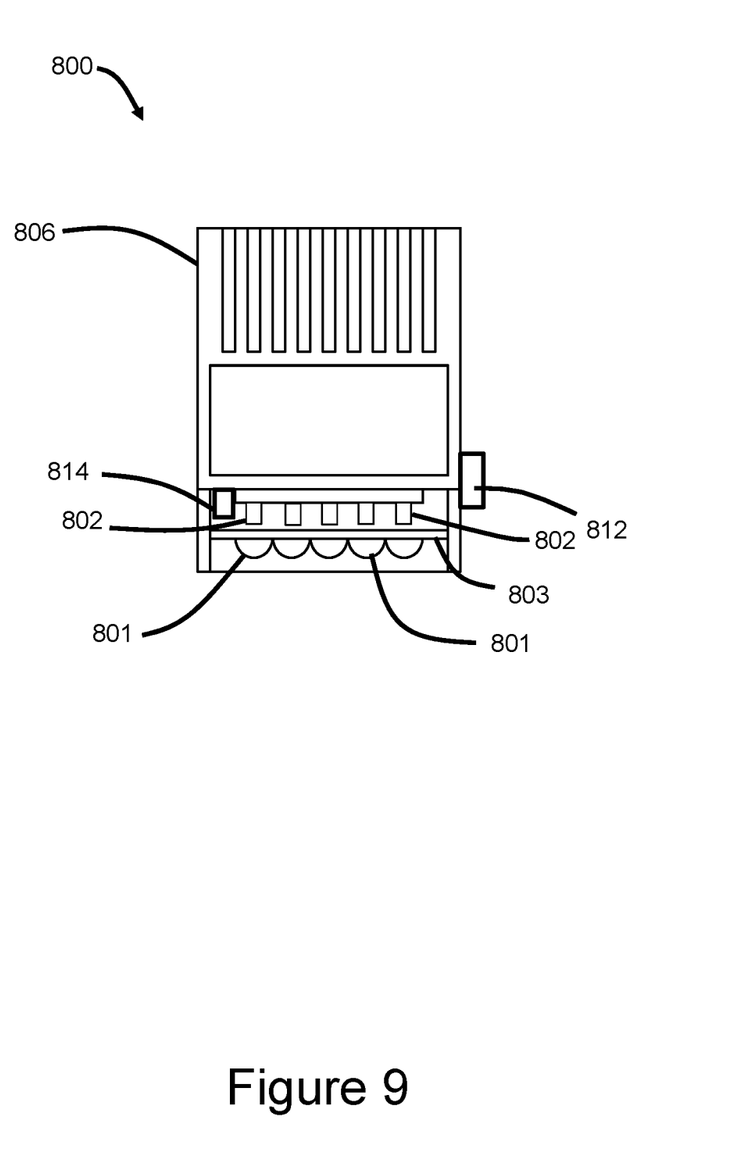

FIGS. 8 and 9 illustrate a track lighting implementation of the luminaire of FIG. 1 in which the beam angle adjustor is implemented by rotating an array of lenses (lenslets) 801 on a base 803 with respect to a fixed array or matrix of LEDs 802. When the lenslets 801 and LEDs 802 are aligned the emitted light beams are parallel. Diverging light beams are emitted when the lenslets 801 and LEDs 802 are not aligned. The illustrated luminaire 800 includes a matrix of LEDs 802 in a housing 806 that pivots and rotates relative to a track mount 808. The housing 806, and thus the LED matrix, may be rotatable through 360 degrees and pivot to some angle, e.g. and without limitation +/−90 degrees, relative to an axis 810 that is normal to the ceiling. A motion sensor 812 and a distance sensor 814 may be incorporated into the housing 806 or LED matrix 802. The luminaire 800 may be aligned with the target surface by swiveling and pivoting the housing 806 to point the matrix of LEDs 802 toward the target surface. The distance sensor 814 may be used both to measure the distance to the target surface and to detect a beam intercept, e.g. by a person, based on a change in the measured distance.

Throughout the entirety of the present disclosure, use of the articles "a" and/or "an" and/or "the" to modify a noun may be understood to be used for convenience and to include one, or more than one, of the modified noun, unless otherwise specifically stated. The terms "comprising", "including" and "having" are intended to be inclusive and mean that there may be additional elements other than the listed elements.

Elements, components, modules, and/or parts thereof that are described and/or otherwise portrayed through the figures to communicate with, be associated with, and/or be based on, something else, may be understood to so communicate, be associated with, and or be based on in a direct and/or indirect manner, unless otherwise stipulated herein.

A number of features, aspects, embodiments and implementations have been described. Nevertheless, it will be understood that a wide variety of modifications and combinations may be made without departing from the scope of the inventive concepts described herein. Accordingly, those modifications and combinations are within the scope of the following claims.

What is claimed is:

1. An apparatus comprising:
   a first light source;
   a beam angle adjustor that controls a beam angle of the first light source and indicates the beam angle;
   a distance sensor that indicates a distance from the first light source to a target surface that is irradiated by the first light source;
   a motion sensor that indicates sensed motion in a volume of space that is greater than a volume of space in which the first light source emits light; and
   a processor configured to:
      calculate and set a radiance of the first light source based on the beam angle indicated by the beam angle adjustor and the distance from the first light source to the target surface indicated by the distance sensor in order to achieve a predetermined irradiance of the target surface;
      partially reduce the radiance of the first light source when the motion sensor detects motion and the distance sensor does not detect a change in the distance; and
      zero the radiance of the first light source when the motion sensor detects motion and the distance sensor detects a change in the distance.

2. The apparatus of claim 1, further comprising a power supply, and wherein the processor is configured to control the power supply to set the radiance of the first light source.

3. The apparatus of claim 1, wherein the first light source is a disinfecting light source comprising a plurality of light emitting diodes (LEDs) that emit at least one of: UV-C radiation (100 nm-280 nm); UV-B radiation (280 nm-315 nm); UV-A radiation (315 nm-400 nm); violet light, and blue light.

4. The apparatus of claim 3, further comprising a power supply, and wherein the processor is configured to control the power supply to selectively power and de-power individual LEDs in the plurality of LEDs of the disinfecting light source.

5. The apparatus of claim 1, further comprising a second light source comprising a plurality of LEDs that emit white light.

6. The apparatus of claim 5, wherein the processor is configured to respond to an indication of motion from the motion sensor to partially reduce the radiance of the first light source and change the second light source from an OFF state to an ON state.

7. An apparatus comprising:
   a first light source that emits disinfecting light;
   a second light source that emits white light;
   a beam angle adjustor that controls a beam angle of the first light source and indicates the beam angle;
   a distance sensor that indicates a distance from the first light source to a target surface that is irradiated by the first light source;
   a motion sensor that indicates sensed motion in a volume of space that is greater than a volume of space in which the first light source emits the disinfecting light; and
   a processor configured to:
      calculate and set a radiance of the first light source based on the beam angle indicated by the beam angle adjustor and the distance from the first light source to the target surface indicated by the distance sensor in order to achieve a predetermined irradiance of the target surface;
      partially reduce the radiance of the first light source when the motion sensor detects motion and the distance sensor does not detect a change in the distance; and
      zero the radiance of the first light source when the motion sensor detects motion and the distance sensor detects a change in the distance.

8. The apparatus of claim 7, wherein in the absence of sensed motion the processor is configured to place the first light source in an ON state and the second light source in an OFF state.

9. The apparatus of claim 8, wherein the processor is configured to respond to an indication of motion from the motion sensor by partially reducing the radiance of the changing of the second light source from an OFF state to an ON state.

* * * * *